United States Patent [19]

Mulder

[11] Patent Number: 5,536,502
[45] Date of Patent: Jul. 16, 1996

[54] SKIN-TEAR MEDICAMENT AND METHOD OF USE

[75] Inventor: Gerit D. Mulder, Englewood, Colo.

[73] Assignee: Gerit D. Mulder, Englewood, Colo.

[21] Appl. No.: 383,507

[22] Filed: Feb. 3, 1995

[51] Int. Cl.$^6$ .............................. A61K 7/40; A61K 7/48
[52] U.S. Cl. ..................... 424/405; 424/401; 514/969
[58] Field of Search .................................. 424/405, 70.1, 424/78.02, 78.06, 78.07, 401; 514/969

[56] References Cited

U.S. PATENT DOCUMENTS

| 4,767,463 | 8/1988 | Brode et al. | 106/162 |
|---|---|---|---|
| 5,110,593 | 5/1992 | Benford | 424/401 |

OTHER PUBLICATIONS

Cosmetic Ingredient Review; Ingredient Publication Status; Jun. 24, 1994; pp. 1–124.

*Primary Examiner*—Thurman K. Page
*Assistant Examiner*—Pamela S. Webber
*Attorney, Agent, or Firm*—Duft, Graziano & Forest

[57] ABSTRACT

A low-sensitizing medicament for use in treating skin-tear injuries includes an emulsified water and hydrocarbon carrier portion, an emollient portion, a hydroxyquinoline antimicrobial portion, a mild keratolytic portion, and a paraben preservative portion. Additional ingredients include a zinc oxide topical protectant, vitamin E, a buffer or alkalizer agent that adjusts pH in a range from 6.5 to 6.8, and a scenting agent.

18 Claims, No Drawings

SKIN-TEAR MEDICAMENT AND METHOD OF USE

BACKGROUND OF THE INVENTION

1. Field of the Invention

The present invention pertains to the field of topical ointments and, more particularly, to products that are used for the treatment of superficial lesions including skin tears. Still more specifically, the medicament includes a carrier component, an emollient component, a cosmetic biocide component, and a mild keratolytic component that will facilitate effective wound site reepithelialization.

2. Description of the Prior Art

Superficial skin injury and skin tears may result in painful and unpleasant lesions that may progress to infection, continued wound deterioration and wound chronicity. Infections are known to be associated with rapid wound deterioration. Exposed, desiccated, and injured tissue may be slow or recalcitrant to healing, particularly in the elderly or medically compromised population.

Skin tears frequently occur in bedridden, medically compromised and institutionalized persons. Healing is frequently delayed and complicated by medical problems, the patient's low-level ambulatory status, and the availability of efficacious treatment modalities. In bedridden and institutionalized persons, tissue damage commonly induces a painful lesion that rapidly desiccates or becomes infected. Factors that may delay healing include, but are not limited to the following items: (1) poor circulation; (2) decreased elastin and collagen production in the skin (i.e., decreased cellular activity associated with healing); (3) bacterial contamination; (4) medications; and (5) extrinsic environmental factors (e.g., shear, pressure, and incontinence).

Current treatment modalities consist of applications of various types of gauze, adhesive synthetic dressings, and antimicrobial ointments. These products are only marginally effective. Furthermore, no products are available which are designed solely and specifically for skin tear injuries.

The U.S. Food and Drug Administration has approved guidelines for the use of cosmetic chemicals that are commonly provided in over-the-counter ointments. These chemicals are submitted to the FDA for over the counter drug review and approval. Approval is indicated by a final publication or report in the form of a monograph. The *Cosmetic Ingredient Review, Ingredient Publication Status* (Jun. 24, 1994) from the Cosmetic & Toiletry Foundation Association in Washington, D.C. provides a list of approved cosmetic chemicals, which is hereby incorporated by reference herein. This publication provides a list of approved cosmetic ingredients, the approved functions for these ingredients, and citations to the corresponding monograph publications for each ingredient. These "cosmetic" ingredients can be used in wound-care products, as well as other products such as lotion, hair dye and the like. The general nature and function is known for each ingredient, but great variations in efficacy can be observed based upon the precise selection of ingredients and the concentration of ingredients. Even within the approved concentration ranges, many of these approved chemicals are known to induce adverse reactions in sensitive patients.

U.S. Pat. No. 5,266,318, issued to Taylor-McCord, teaches the use of an anthraquinone-free cold processed fresh aloe vera extract for treatment of wounds to the skin. Aloe vera gel is described as a mucilaginous jelly from the parenchymal cells of the aloe plant. This jelly includes about 98.5% water with about 60% of the total solid being made up of polysaccharides, and the balance including organic acids and inorganic compounds. It is noted that a present controversy exists over the precise curative agent that is found in aloe vera, but the gel is generally acknowledged to have an ability to reduce swelling and irritation. This therapeutic benefit may be partially offset by cytotoxic activity of the yellow sap and aloin portions of the gel.

U.S. Pat. No. 5,110,593, issued to Benford, describes a topical ointment for use in treating diaper dermatitis. An antimicrobial agent consisting of 0.22% 8-hydroxyquinoline is combined with petrolatum, lanolin, beeswax, sodium borate, lanolin alcohols, methyl salicylate, sorbitan sesquioliate, methylparaben, propylparaben, and trisodium HESTA. This substance is free of keratolytic ingredients such as allantoin and urea.

There remains a need for a non-irritating, topical ointment or medicament that is specifically designed to promote the reepithelialization of skin tears.

SUMMARY OF THE INVENTION

The present invention overcomes the problems that are outlined above by providing a non-sensitizing over the counter topical wound care medicament that is specially formulated to assist reepithelialization of skin tear injuries. The ingredients combine to provide emollient, humectant, and mild keratolytic activities that mutually facilitate and expedite the healing process.

Broadly speaking, the medicament includes an emulsified carrier portion, an emollient portion, a humectant portion, a cosmetic biocide portion, and a keratolytic portion, all combined in effective amounts for assisting reepithelialization of skin-tear injuries. The carrier ingredients may be selected to adjust a viscosity of the medicament for use with an intended delivery system. For example, the liquid may be delivered as a spray-on liquid or a spread-on balm.

In preferred forms of the invention, a preservative portion is provided in a substantially non-sensitizing concentration to improve the shelf-stability of the medicament. Additional ingredients may also be added to promote healing, e.g., a zinc oxide topical protectant or vitamin E in an effective amount to promote healing. As needed, an emulsion stabilizer portion may be added to prolong the shelf life of the stable emulsion product.

The emulsified carrier portion preferably provides from 50% to 70% of the total medicament weight ("w/w"). This portion preferably contains water and least one hydrocarbon emulsified with the water. Spray-on liquid medicaments preferably include from 45% to 50% water, 0.5% to 1.5% aloe vera gel; 8% to 12% mineral oil gel, and 0.5% to 1.5% beeswax, all determined as percentages of the total medicament weight ("w/w"). The spray-on liquid carrier portion most preferably includes about 48% water, 1% aloe vera gel, 10% mineral oil gel, and 1% beeswax. Spread-on gel carriers preferably include from 35% to 45% petrolatum and from 20% to 35% water, and most preferably include about 28% water with about 35% petrolatum.

The emollient portion preferably provides from about 5% to 25% of the total medicament weight, and more preferably from 5% to 11%. This latter portion preferably includes 0.5 to 1.5% lanolin oil, 4% to 6% octyl palmitate, and 1% to 3% isopropyl lanolate, (w/w), for use in spray-on medicaments. Most preferably, this portion includes about 5% glycerine, 1% lanolin oil, 5% octyl palmitate, and 2% isopropyl lanolate (w/w), for use in spray-on medicaments. Alternatively, the emollient portion more preferably includes from 10% to 20% lanolin oil for use in spread-on gel medicaments.

The humectant portion is preferably glycerine in an amount that ranges from 12% to 17% of the total medicament weight. Other suitable humectants include ethoxylated glucose derivatives, such as Methyl Gluceth-10 (CTFA adopted name).

The cosmetic biocide is most preferably 8-hydroxyquinoline (generally, "oxyquinoline") in an amount up to about 2.7% of the total medicament weight and, most preferably, up to about 0.8%. At higher concentrations than about 2% to 3% by weight, 8-hydroxyquinoline increasingly becomes a sensitizing agent that may inhibit wound healing processes. Lower concentrations of about 0.8% may provide sufficient biocidal activity to inhibit the microbial production of odors.

The mild keratolytic portion preferably provides no more than about 10% of the medicament weight. More preferably, the mild keratolytic portion is kept below 1% by weight because this concentration provides a tissue softening function without inducing rampant tissue breakdown and exfoliation. Accordingly, physical debridement of the wound site is facilitated, but substantial debridement (e.g., exfoliation) is not directly induced by keratolytic action. Additionally, it is believed that the tissue-softening function of these lower concentrations will enhance the action of the emollient and humectant portions of the medicament. The preferred keratolytic agents are urea and allantoin. The keratolytic portion of spray-on medicaments preferably contains from 0.3% to 0.8% allantoin, and 0.05% to 0.15% urea (w/w). The most preferred spray-on keratolytic portion contains 0.5% allantoin and 0.1% urea (w/w).

The preservative portion preferably provides up to about 0.5% of the medicament weight. Particularly preferred preservatives include sodium ethylenediaminetetraacetate ("EDTA") and the alkyl parabens (e.g., methyl, ethyl, propyl, and butyl). More preferably, this portion contains from 0.03% to 0.08% EDTA, and from 0.2% to 0.4% alkyl paraben (w/w). The most preferred preservative portion contains 0.05% EDTA and 0.3% methylparaben. Effective preservatives typically also function as sensitizing agents. Parabens and EDTA are particularly preferred for their mild sensitizing effect. Optionally, where preservative sensitivity is a concern, the medicament may be packaged in sterile single use containers that avoid the need for sensitizing-preservatives.

It is preferred to provide the emulsion stabilizer portion only as needed to stabilize the emulsified product. Preferred emulsion stabilizers include lanolin waxes and/or alcohols, and sorbitan sesquioliate. A typical stabilizer portion will include 0.2% to 0.4% lanolin alcohols and 0.2% to 0.3% sorbitan sesquioliate (w/w). Other stabilizers such as 3% stearic acid may be added (w/w). The use of emulsion stabilizers should be minimized because these materials can also act as sensitizing agents.

DETAILED DESCRIPTION OF THE PREFERRED EMBODIMENT

Clinical experience has confirmed that substantial improvements in the efficacy of wound-care products can be obtained by: (1) preventing desiccation of the wound site; (2) reducing microbial action at the wound site; (3) eliminating non-viable cells and waste products from the wound site; (4) reducing the need for physical debridement of the wound site; and (5) reducing or eliminating sensitizing agents in wound care products that cause inflammation or other irritation. Treatment methodology following these points can greatly expedite the healing of skin-tear injuries. Nevertheless, no one single commercial product exists that performs all of these functions. The present invention presents a combination of ingredients that provide the above-described multifaceted treatment.

The present medicament has ingredients that can be divided into a number of functional groups which compliment one another to facilitate reepithelialization. The combined ingredients provide a humectant function that stabilizes moisture at the wound site, a mild keratolytic function that facilitates the softening of tissue, an emollient function that softens or soothes dried skin, a cosmetic biocide function that reduces microbial action at the wound site, an enzymatic assist function that promotes tissue regrowth, and a pH control function that provides an optimal environment for regrowth. Accordingly, patient discomfort is minimized while the multifunctional medicament works to expedite the healing process.

Significant percentages of patients have adverse reactions (e.g., discomfort and poor reepithelialization progress) to sensitizing agents. Sensitizing agents are hereby defined as those that induce chemical burns or allergic reactions in at least some persons. Common sensitizing agents, e.g., dexpanthenol, chlorides, chamomile, propylene glycol, and lanolin alcohols, are preferably avoided. Substantial improvements in wound-care efficacy may be observed in wound-care products having reduced contents of these sensitizing agents. The ingredients of the present medicament, accordingly, minimize the content of sensitizing agents. In contrast, prior practices have been to include such chemicals in small amounts for their perceived benefits.

The preferred medicament includes respective functional portions of ingredients, i.e., carrier, emollient, cosmetic biocide, mild keratolytic, and non-irritating preservative portions. Each of these portions preferably incorporate a plurality of ingredients that each perform a function of the same general nature, but the different materials are not purely redundant in that each ingredient affects skin tissue in different ways.

The emulsified carrier portion is formed of a water and hydrocarbon emulsion wherein the immiscible phases dissolve or carry like materials. The hydrocarbon is preferably mineral oil gel or petrolatum. Mineral oil gel is a polyoxyalkylated form of mineral oil having a relatively thicker consistency that is useful for spray-on medicaments. Petrolatum is thicker still, and is more suitable for use in spread-on medicaments.

The emollient portion preferably includes ingredients such as glycerine, lanolin or lanolin oil, octyl palmitate, isopropyl lanolate, and mixtures thereof. These ingredients all provide soothing emollient action by lubricating injured skin. Additionally, these ingredients perform a humectant function by stabilizing the water content of tissues at the wound site. Each emollient has a different mobility or activity level to provide a combined efficacy over a variety of environmental conditions. The stabilization of wound-site water content is particularly advantageous in preventing the consequential death of healthy skin cells through desiccation, and promoting the migration of epithelial cells. These topical emollients are selected in the applied concentrations because they serve to maintain wound-site cellular water concentrations within acceptable levels, but remain outside the skin cell walls.

The mild keratolytic portion preferably includes urea and/or allantoin, which soften wound-site tissues to enhance the effect of the emollient and humectant portions. This mutual softening action also facilitates physical wound debridement activities, if needed. Furthermore, the low concentration of the mild keratolytic portion is low enough to prevent noticeable sensitization of the wound site.

Reepithelialization occurs most effectively in an environment having a slightly acidic pH, i.e., one ranging from about 6.5 to 6.8. This environment simultaneously fosters the migration and growth of new epithelial cells while inhibiting bacterial growth. Without pH adjustment, the preferred ranges of ingredients can have a pH below 6.5. Accordingly, it is preferred to adjust the pH by adding a compatible alkalizer in an effective amount for obtaining a pH value within the preferred range. Particularly preferred alkalizers include triethanolamine at a concentration of up to about 1% (w/w), or sodium borate at a concentration of up to about 1% (w/w). Alternatively, a compatible acid and conjugate base buffer system may be utilized to hold the pH at slightly acidic values.

The following non-limiting examples set forth preferred materials and methods for practicing the present invention.

EXAMPLE 1

Spray Liquid Medicament

The ingredients listed in Table 1 below can be acquired from commercial sources and mixed in the weight percentages indicated to provide a spray-on liquid composition. The ingredients are vigorously mixed to form an emulsion.

TABLE 1

| Medicament Portion | Ingredient | Weight (%) |
|---|---|---|
| Carrier | Deionized Water | 47.80 |
| | Aloe Vera Gel | 1.00 |
| | Mineral Oil Gel | 10.00 |
| | Beeswax | 1.00 |
| *** | Carrier Subtotal | *59.80 |
| Humectant | Glycerine 96% | *13.50 |
| | Lanolin Oil | 9.50 |
| | Octyl Palmitate | 5.00 |
| | Isopropyl Lanolate | 2.00 |
| *** | Emollient Subtotal | *16.50 |
| Keratolytic | Allantoin | 0.50 |
| | Urea | 0.10 |
| *** | Keratolytic Subtotal | *0.60 |
| Odor-Reducing Agent | Hydroxyquinoline | *0.75 |
| Preservative | Trisodium EDTA | 0.05 |
| | Methylparaben | 0.30 |
| *** | Preservative Subtotal | *0.35 |
| Topical Protectant | Zinc Oxide | *2.00 |
| Scenting Agent | Methyl Salicylate | *0.25 |
| Emulsion Stabilizer | Sorbitan Sesquioleate | 0.25 |
| | Stearic Acid | 3.00 |
| | Lanolin Derivative Wax | 0.30 |
| *** | Emulsion Stabilizer Subtotal | *3.55 |
| Vitamin E | α-tocopherol | *1.00 |
| Alkalizer | Sodium borate | *1.00 |
| Pigment Wetting Agent | Isopropyl esters of fatty acids (e.g., Amerlate P from Amerchol) | *0.70 |
| | Total | 100.00 |

The resultant medicament is a low viscosity, shelf-stable emulsion of pH 6.5 that can be applied to a wound site through the use of a conventional spray bottle apparatus. The mechanical action of spray liquid permits a complete flushing of the wound site to soften and rinse away debris from the wound, thereby minimizing the need for physical scrubbing to debride the wound. Treatment is performed as needed, and is suggested three to four times per day with the frequency of application decreasing as the wound heals. The viscosity of the medicament is low enough to permit spray application, yet high enough to prevent substantial free liquid runoff subsequent to application.

EXAMPLE 2

Gel Balm Ointment

The ingredients listed in Table 2 below can be acquired from commercial sources and mixed in the weight percentages indicated to provide a spreadable gel balm composition. The ingredients are vigorously mixed to form an emulsion.

TABLE 2

| Medicament Portion | Ingredient | Weight (%) |
|---|---|---|
| Carrier | Deionized water | 27.72 |
| | Petrolatum | 34.90 |
| | Beeswax | 5.84 |
| *** | Carrier Portion Subtotal | *68.46 |
| Emollient | Lanolin Oil | *15.5 |
| Preservative | Methylparaben | 0.25 |
| | Propylparaben | 0.10 |
| *** | Preservative Subtotal | *0.35 |
| Cosmetic Biocide | 8-hydroxyquinoline | *0.75 |
| Topical Protectant | Zinc Oxide | *2.00 |
| Scenting Agent | Methyl Salicylate | *0.25 |
| Vitamin E | α-tocopherol | *1.00 |
| Alkalizer | Sodium Borate | *0.94 |
| Emulsion Stabilizer | Sorbitan Sesquioleate | *0.25 |
| | Lanolin Derivative Wax | *0.50 |
| *** | Emulsion Stabilizer Subtotal | *0.75 |
| Keratolytic Portion | Urea | *10.00 |
| | Total | 100.00 |

The resultant medicament or ointment is a high viscosity, shelf-stable, gel-like emulsion that can be spread over a wound site. The application of gel to the wound reduces the need for repeat applications throughout the course of a day, and provides an enhanced emollient action by protecting skin tissue from desiccation due to atmospherically-induced evaporation losses. Some physical disturbance of the wound site is demanded to remove the old gel prior to successive applications. The 10% urea concentration is generally too high for use in open wounds, and is preferably kept below 1%. This second example, accordingly, is less preferred than the product of Example 1. If less substantial keratolytic activity is desired, the urea content may be reduced to the level of Table 1 or completely left out of this formulation. In compensation for the reduced urea content, the water and petrolatum portions can be adjusted proportionately upward.

Those skilled in the art will understand that the preferred embodiments described above may be subjected to obvious modifications without departing from the true scope and spirit of the invention. Accordingly, the inventors hereby state their intention to rely upon the Doctrine of Equivalents to protect their full rights in the invention.

I claim:

1. A non-irritating medicament for use in treating skin-tear wounds, comprising:

an emulsified carrier portion comprising water and at least one hydrocarbon emulsified with said water, said carrier portion having a weight ranging from about 50% to 70% of a total medicament weight;

an emollient portion having a weight ranging from about 5% to 25% of the total medicament weight;

a humectant portion having a weight ranging from about 12% to 17% of the total medicament weight;

a cosmetic biocide portion including oxyquinoline in a weight up to 3% of the total medicament weight; and a keratolytic portion having a weight less than about 10% of the total medicament weight.

2. The medicament as set forth in claim 1, said carrier portion consisting essentially of from 45% to 50% water, 0.5% to 1.5% aloe vera gel; 8% to 12% mineral oil gel, and 0.5% to 1.5% beeswax, determined as percentages of the total medicament weight.

3. The medicament as set forth in claim 2, further comprising a pH adjusting agent in an effective amount for adjusting a pH of the medicament within a range from 6.5 to 6.8.

4. The medicament as set forth in claim 3, said pH adjusting agent comprising sodium borate in an amount up to about 2% of the total medicament weight.

5. The medicament as set forth in claim 1, said emollient portion consisting essentially of 0.5 to 1.5% lanolin oil, 4% to 6% octyl palmitate, and 1% to 3% isopropyl lanolate, determined as percentages of the total medicament weight.

6. The medicament as set forth in claim 1, said humectant portion consisting essentially of 12% to 17% glycerine determined as a percentage of the total medicament weight.

7. The medicament as set forth in claim 1, said keratolytic portion consisting essentially of 0.3% to 0.8% allantoin, and 0.05% to 0.15% urea, determined as percentages of the total medicament weight.

8. The medicament as set forth in claim 1, said preservative portion consisting essentially of from 0.03% to 0.08% trisodium EDTA, and from 0.2% to 0.4% alkyl paraben, determined as percentages of the total medicament weight.

9. The medicament as set forth in claim 1, said medicament having a pH ranging from about 6.5 to 6.8.

10. The medicament as set forth in claim 1, said medicament being essentially free of sensitizing agents comprising dexpanthenol, chlorides, chamomile, and propylene glycol.

11. The medicament as set forth in claim 1 further comprising about 1% vitamin E.

12. The medicament as set forth in claim 1, further comprising a preservative portion selected from a group consisting of alkyl parabens, EDTA, and mixtures thereof, said preservative portion providing up to about 0.5% of the total medicament weight.

13. The medicament as set forth in claim 1, said carrier portion comprising from 35% to 45% petrolatum and from 20% to 35% water, determined as percentages of the total medicament weight.

14. The medicament as set forth in claim 13, said emollient portion comprising a lanolin oil in a weight ranging from about 10% to 20% of the total medicament weight.

15. The medicament as set forth in claim 14, wherein said keratolytic portion includes 10% urea determined as a percentage of the total medicament weight.

16. A method of treating skin tear wounds, said method comprising the steps of:

providing a medicament comprising an emulsified carrier portion comprising water and at least one hydrocarbon emulsified with said water, said carrier portion having a weight ranging from about 50% to 70% of a total medicament weight;

an emollient portion having a weight ranging from about 5% to 30% of the total medicament weight;

a humectant portion having a weight ranging from about 12% to 17% of the total medicament weight;

a cosmetic biocide portion comprising oxyquinoline in a weight up to 2.7% of the total medicament weight; and a keratolytic portion having a weight up to about 10% of the total medicament weight; and applying said medicament to a skin tear injury to produce applied medicament.

17. The method as set forth in claim 16, said medicament being in a spray-on liquid form, wherein said applying step includes a step of spraying said medicament onto said injury.

18. A non-irritating medicament for use in treating skin-tear wounds, consisting essentially of:

an emulsified carrier portion including water, aloe vera gel, and mineral oil gel, said carrier portion having a weight ranging from about 50% to 70% of a total medicament weight;

an emollient portion including lanolin, octyl palmitate, and isopropyl lanolate, in a combined weight ranging from about 5% to 25% of the total medicament weight;

a glycerine portion having a weight ranging from about 12% to 17% of the total medicament weight;

a cosmetic biocide portion including oxyquinoline; and a keratolytic portion including allantoin and urea in a weight less than about 10% of the total medicament weight, said medicament being essentially free of sensitizing agents including dexpanthenol, chlorides, and propylene glycol.

\* \* \* \* \*